United States Patent

Oakes et al.

[11] Patent Number: 5,241,077
[45] Date of Patent: Aug. 31, 1993

[54] PEROXYACIDS

[75] Inventors: John Oakes; David W. Thornthwaite, both of Cheshire, England

[73] Assignee: Lever Brothers Company, Division of Conopco, Inc., New York, N.Y.

[21] Appl. No.: 854,282

[22] Filed: Mar. 20, 1992

[30] Foreign Application Priority Data

Mar. 21, 1991 [GB] United Kingdom ............... 9105959

[51] Int. Cl.$^5$ ........................................ C07D 209/48
[52] U.S. Cl. .................................................. 548/477
[58] Field of Search .................... 548/477; 252/186.26

[56] References Cited

U.S. PATENT DOCUMENTS

| | | | |
|---|---|---|---|
| 4,634,551 | 1/1987 | Burns et al. | 252/102 |
| 4,686,063 | 8/1987 | Burns | 252/102 |
| 5,061,807 | 10/1991 | Gethoffer et al. | 548/473 |
| 5,098,598 | 3/1992 | Sankey et al. | 252/186.42 |
| 5,106,528 | 4/1992 | Francis et al. | 252/186.23 |

FOREIGN PATENT DOCUMENTS

| | | |
|---|---|---|
| 0316809 | 5/1989 | European Pat. Off. |
| 0325288 | 7/1989 | European Pat. Off. |
| 0325289 | 7/1989 | European Pat. Off. |
| 0349940 | 1/1990 | European Pat. Off. |
| 0366041 | 5/1990 | European Pat. Off. |
| 0435379 | 7/1991 | European Pat. Off. |
| 3906768 | 9/1990 | Fed. Rep. of Germany. |
| 9007501 | 7/1990 | PCT Int'l Appl. |
| 9109843 | 7/1991 | PCT Int'l Appl. |

*Primary Examiner*—Joseph Paul Brust
*Assistant Examiner*—Jacqueline Haley
*Attorney, Agent, or Firm*—Milton L. Honig

[57] ABSTRACT

Cationic peroxycarboxylic acids having the general formula (I)

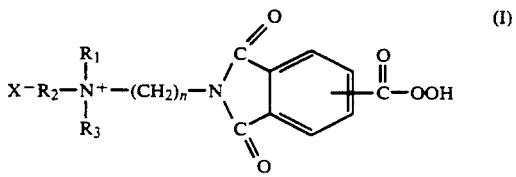

wherein $R_1$, $R_2$ and $R_3$ are each independently a $C_1$-$C_7$ alkyl group or $C_1$-$C_7$ substituted alkyl group, n is an integer of from 2 to 10 and X is a counter anion. The peroxycarboxylic acids may be used in bleaching and detergent compositions.

4 Claims, No Drawings

PEROXYACIDS

This invention relates to novel cationic peroxyacids which are non-explosive. The invention also relates to bleaching and detergent compositions comprising said peroxyacids.

More particularly, the invention relates to cationic peroxycarboxylic acids having the general formula (I):

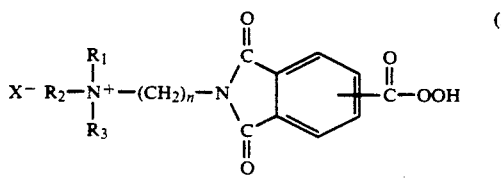

wherein $R_1$, $R_2$ and $R_3$ are each independently a $C_1-C_7$ alkyl or $C_1-C_7$ substituted alkyl group, n is an integer of from 2 to 10, and $X^-$ is a counter anion.

Preferred compounds of this class are those wherein the

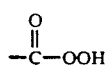

group is substituted on the aromatic ring in the meta-position with respect to the phthalimido group i.e. compounds of general formula (I').

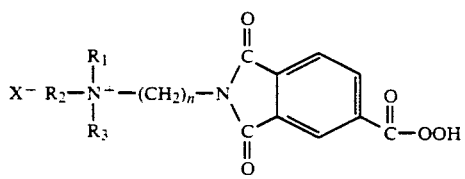

The peroxyacids of the above formulae (I) and (I') are new compounds which constitute a class of products which are highly interesting from an industrial point of view. Like peroxyacids which have previously been described they may find use in many industrial applications and processes, e.g. in the field of plastics as polymerisation initiators or as oxidants for olefin epoxydation, and in many other oxidative processes in the field of e.g. fine chemicals, and in bleaching processes.

Specifically, the peroxyacids of the above formulae find particular application in the field of bleaching in the detergent industry.

Recently, organic peroxyacids have attracted increasing interest in industry. This is especially due to their bleaching activity in detergent and/or bleaching formulations for use at medium to low temperature such as medium to low temperature washing processes. The ability to show bleaching action at low temperatures is particularly important because of the need to save energy. There are also technical advantages in using peroxyacids in preference to peroxyacid precursors and a hydrogen peroxide source, such as sodium perborate. Peroxyacids are:

a) insensitive to the deleterious effects of catalase; and
b) have greater formulation flexibility and, unlike peroxyacid precursors, can be formulated at their optimum bleach potential with savings in formulation space.

A large number of organic peroxyacids have been described which are endowed with the required properties of high bleaching activity. Many (cyclo) aliphatic and aromatic mono- or diperoxy carboxylic acids are already known and proposed for use in amongst others, the field of detergents. Examples of such materials include diperoxydodecanedioic acid (DPDA), diperoxyazelaic acid (DPAA), diperoxybrazilic acid (DPBA), and the substituted or unsubstituted diperoxyglutaric acid (DPGA).

Though these peroxyacids indeed show satisfactory bleach performance at medium to low temperatures, they are not sufficiently stable to explosion.

Recently a new class of imido-(aromatic) peroxy-carboxylic acids have been described in EP-A-0 325 288 and EP-A-0 349 940 which are purportedly more stable and less prone to explosions. One particular representative thereof is phthalimido-peroxyhexanoic acid (PAP), which has the following structural formula (II):

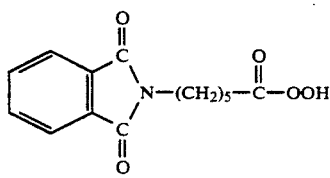

The pKa of these peroxyacids generally lies between values of about 7-8.2, which means bleaching performance is poor at the normally high wash pH range of about 9-10.

The present invention relates to cationic peroxy carboxylic acids which are more effective bleaching agents than the above described conventional (anionic) peroxyacids. Though cationic peroxyacids are also known in the art e.g. from EP-A-0 316 809 (Ausimont), the problem with such compounds is the risk of explosion.

It is an object of the invention to mitigate the above drawbacks to a substantial degree.

Another object of the invention is to provide a bleaching and/or detergent composition comprising a peroxycarboxylic acid.

These and other objects will be clear from the following description of the invention.

Accordingly, the invention provides a cationic peroxycarboxylic acid having the general formula (I), as hereinbefore defined.

Preferably, the cationic peroxycarboxylic acid has the general formula (I'), as hereinbefore defined.

With respect to these formulae, $R_1$, $R_2$ and $R_3$ are preferably each independently a $C_1-C_4$ alkyl group, more preferably methyl or ethyl, and most preferably methyl. Preferably n is from 2 to 5. $X^-$ may be any suitable counter anion, such as $Cl^-$, $Br^-$, $NO_3^-$, $HSO_4^-$, $SO_4^{2-}$, $CH_3SO_4^-$, or any other surfactant anion e.g. alkylbenzene sulphonate.

Particularly preferred cationic peroxycarboxylic acids of the invention are thus compounds of the formula:

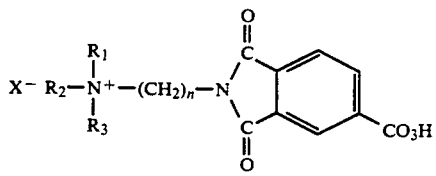

wherein R is methyl or ethyl and n=2 to 5, particularly preferred peroxycarboxylic acids are those wherein n=3 and R=methyl:

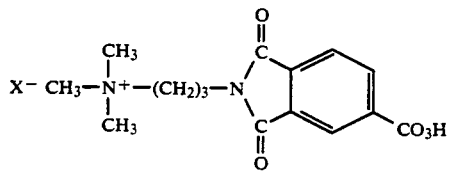

(trimethyl ammonium propenyl imidoperoxy-mellitic acid).

The compounds of the present invention can be referred to as cationic imido aromatic peroxy carboxylic acids.

Their properties, namely they
i) are non-explosive
ii) have good bleach performance over a broad pH range, such as from pH 2 to 12; and
iii) can be prepared in high state of purity, means they may readily be employed in a variety of industrial applications. In particular, they may be used as bleaching or cleaning agents in washing, cleaning and disinfecting compositions, such as laundry detergents, laundry bleaches, hard surface cleaners, toilet bowl cleaners, automatic dishwashing composition, denture cleaners and other sanitising compositions.

The peroxycarboxylic acids of the invention may readily be prepared by reaction of an diamine of formula (V),

wherein $R_1$ and $R_2$ and are each independently a $C_1$-$C_7$ alkyl or $C_1$-$C_7$ substituted alkyl group and n is an integer of from 2 to 10, with an appropriate anhydride, followed by quaternisation and peroxidation.

The compound of formula (IV) for example may be prepared by reaching trimellitic anhydride with dimethylamino-propylamine, both relatively inexpensive materials, followed by quaternisation with dimethylsulphate and peroxidation.

As explained above, the cationic peroxycarboxylic acid of the invention can be used as a highly effective bleach component in detergent compositions, which compositions are particularly suitable for use at low to medium wash temperatures, e.g. from 20° C. to 60° C.

Accordingly, another aspect of the invention provides a bleaching composition and a low to medium temperature bleach detergent composition comprising an effective amount of a cationic peroxycarboxylic acid compound of formula (I) as the bleach component.

The term "effective amount. as used herein means that the cationic peroxycarboxylic acid is present in a quantity such that it is operative for its intended purpose, ie as a bleaching agent, when the detergent composition is combined with water to form an aqueous medium which may be used to wash and clean clothes, fabrics and other articles.

The peroxycarboxylic acid which may act as the bleach component of the invention may be incorporated in bleach detergent compositions in amounts of from about 0.5 to 15% by weight, preferably from 2 to 10% by weight.

The bleach detergent compositions of the invention will contain at least one surface-active compound, which may be anionic, cationic, nonionic or amphoteric in character, which will generally be present at a level from about 3 to about 40%, preferably from 5 to 35% by weight.

Generally, mixtures of the above surface-active compounds are used. In particular, mixtures of anionic and nonionic surface-active compounds are commonly used.

The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are water-soluble alkali metal salts of organic sulphates and sulphonates having alkyl radicals containing from about 8 to about 22 carbon atoms, the term alkyl being used to include the alkyl portion of higher aryl radicals.

Examples of suitable synthetic anionic detergent compounds are sodium and ammonium alkyl sulphates, especially those obtained by sulphating higher ($C_8$-$C_{18}$) alcohols produced, for example, from tallow or coconut oil; sodium and ammonium alkyl ($C_9$-$C_{20}$) benzene sulphonates, particularly sodium linear secondary alkyl ($C_{10}$-$C_{15}$) benzene sulphonates; sodium alkyl glyceryl ether sulphates, especially those esters of the higher alcohols derived from tallow or coconut oil, oxo-alcohols and synthetic alcohols derived from petroleum; sodium coconut oil fatty acid monoglyceride sulphates and sulphonates; sodium and ammonium salts of sulphuric acid esters of higher ($C_9$-$C_{18}$) fatty alcohol alkylene oxide, particularly ethylene oxide, reaction products; the reaction products of fatty acids such as coconut fatty acids esterified with isethionic acid and neutralized with sodium hydroxide; fatty acid ester sulphonates; sodium and ammonium salts of fatty acid amides of methyl taurine; alkane monosulphonates such as those derived by reacting alpha-olefins ($C_8$-$C_{20}$) with sodium bisulphite and those derived by reacting paraffins with $SO_2$ and $Cl_2$ and then hydrolyzing with a base to produce a random sulphonate; sodium and ammonium $C_7$-$C_{12}$ dialkyl sulphosuccinates; and olefin sulphonates, which term is used to describe the material made by reacting olefins, particularly $C_{10}$-$C_{20}$ alpha-olefins, with $SO_3$ and then neutralizing and hydrolyzing the reaction product. The preferred anionic detergent compounds are sodium ($C_{11}$-$C_{15}$) alkylbenzene sulphonates, sodium ($C_{16}$-$C_{18}$) alkyl sulphates and sodium ($C_{16}$-$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$-$C_{22}$) phenols, generally 5-25 EO, i.e. 5-25 units of ethylene oxides per molecule;

the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, sugar esters, long chain tertiary amine oxides, long chain tertiary phosphine oxides and dialkyl sulphoxides.

Amounts of amphoteric or zwitterionic surface-active compounds may also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As stated above, soaps may also be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which are used are preferably the sodium, or, less desirably, potassium salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 10%, are used to give a beneficial effect on detergency. This is particularly valuable in compositions used in hard water when the soap acts as a supplementary builder.

The detergent compositions of the invention will normally also contain a detergency builder. Builder materials may be selected from calcium sequestrant materials, precipitating materials, calcium ion-exchange materials; and mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; tartrate mono- and di-succinates; and polyacetal carboxylates as Examples of precipitating builder materials include sodium orthophosphate, sodium carbonate and long chain fatty acid soaps.

Examples of calcium ion-exchange builder materials include the various types of water-insoluble crystalline or amorphous aluminosilicates, of which zeolites are the best known representatives.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxymethyloxy malonate, carboxymethyloxy succinate and the water-insoluble crystalline or amorphous aluminosilicate builder materials, or mixtures thereof.

These builder materials may be present at a level of, for example, from 5 to 80% by weight, preferably from 10 to 60% by weight.

The detergent compositions of the invention may also contain any of the conventional additives in the amounts in which such materials are normally employed in fabric washing detergent compositions. Examples of these additives include lather boosters, such as alkanolamides, particularly the monoethanol amides derived from palmkernel fatty acids and coconut fatty acids, lather depressants, such as alkyl phosphates and silicones, anti-redeposition agents, such as sodium carboxymethyl cellulose and alkyl or substituted alkyl cellulose ethers, stabilizers, such as the various organic phosphonates known under the Trade name "Dequest" and ethylene diamine tetraacetic acid, fabric softening agents, inorganic salts, such as sodium sulphate, and, usually present in very small amounts, fluorescent agents, perfumes, enzymes, such as proteases, cellulases, lipases and amylases, germicides and colourants.

Other useful additives are polymeric materials, such as polyacrylic acid, polyethylene glycol and the copolymers of (meth)acrylic and maleic acid, which may also be incorporated to function as anti-redeposition agents and/or as auxiliary builders together with any of the principal detergency builder or builder mixtures, such as polyphosphates, carbonates, citrates, aluminosilicates and the like. Such a polymeric additive is usually present at a level from about 0.1% to about 0.3% by weight.

The cationic peroxycarboxylic acids of the present invention may be used in a variety of product forms including powders, on sheets or other substrates, in pouches, in tablets or in non-aqueous liquids, such as liquid nonionic detergent composition.

Generally, for reasons of better stability and easy handling, the peroxyacid will advantageously be presented in the form of particulate bodies comprising said peroxyacid bleach and a binder or agglomerating agent. Many diverse methods of preparing such particulates have been described in various patent literature documents, such as e.g. in GB Patent 1,561,333; U.S. Pat. No. 4,087,369; EP-A-0,240,057; EP-A-0,241,962; EP-A-0,101,634 and EP-A-0,062,523. Each of these methods may be selected and applied to the peroxycarboxylic acids of the invention.

When used in a detergent composition, particulates incorporating the cationic peroxyacids of the invention are normally added to the base detergent powder composition in a dry-mixing process. It will be appreciated, however, that the detergent base composition to which the peroxyacid particles are added may itself be made in a variety of ways, such as spray-drying, high energy mixing/granulation, dry-mixing, agglomeration, extrusion, flaking etc., such ways being well known to those skilled in the art and not forming part of the present invention.

The peroxycarboxylic acid of the present invention may also be incorporated in detergent additive products. Such additive products are intended to supplement or boost the performance of conventional detergent compositions and may contain any of the components of such compositions, although they will not comprise all of the components present in a fully formulated detergent composition.

Additive products in accordance with this aspect of the invention may comprise the cationic peroxycarboxylic acid alone in combination with a carrier, such as a compatible particulate substrate, a flexible non-particulate substrate or a container (e.g. pouch or sachet).

Examples of compatible particulate substrates include inert materials, such as clays and other aluminosilicates including zeolites both of natural and synthetic of origin. Other compatible particulate carrier materials include hydratable inorganic salts, such as phosphates, carbonates and sulphates.

Additive products enclosed in bags or containers can be manufactured such that the containers prevent egress of their contents when dry but are adapted to release their contents on immersion in an aqueous solution.

In a further specific embodiment, the peroxyacid of the invention can be suitably incorporated in so-called non-aqueous liquid laundry detergent compositions to impart an effective cleaning and stain-removing capacity to the products on fabrics and textiles.

Non-aqueous liquid detergent compositions including paste-like and gelatinous detergent compositions are known from the art and various formulations have been proposed, e.g. in U.S. Pat. Nos. 2,864,770; 2,940,938; 4,772,412; 3,368,977; GB-A-1,205,711; 1,270,040; 1,292,352; 1,370,377; 2,194,536; DE-A-2,233,771; and EP-A-0,028,849.

These are compositions which normally comprise a non-aqueous liquid medium with or without a solid phase dispersed therein. The non-aqueous liquid medium may be a liquid surfactant, preferably a liquid nonionic surfactant; a non-polar liquid medium, e.g. liquid paraffin; a polar solvent, e.g. polyols, such as glycerol, sorbitol, ethylene glycol, optionally combined with low-molecular monohydric alcohols, e.g. ethanol or isopropanol; or mixtures thereof.

The solid phase can be builders, alkalis, abrasives, polymers, clays, other solid ionic surfactants, bleaches, fluorescent agents and other usual solid detergent ingredients.

The invention will now be illustrated by way of the following examples.

EXAMPLES

The cationic peroxycarboxylic acid of formula (IV) was prepared as follows.

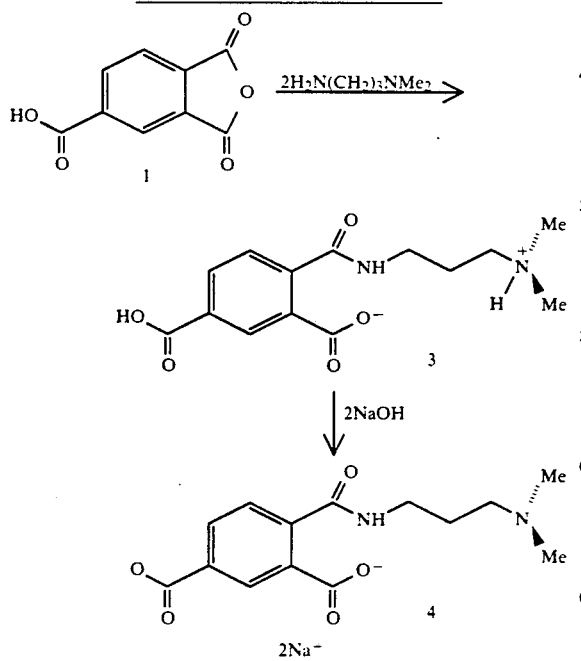

DESCRIPTION OF PROCESS 3 dimethylaminopropylamine (64.26 g, 0.63 mol) was dissolved in water (150 mls) at room temperature. To the resulting solution solid 1,2,4 benzenetricarboxylic anhydride (1) (57.6 g, 0.3 mol) was added in portions with vigorous stirring. The temperature rose to 47° C. After cooling to room temperature, stirring was continued for 1½ hours. The pH of the solution was 9.2. Thereafter sodium hydroxide solution (24 g, 0.6 mol) in 100 mls of water was added with stirring. The pH rose to 12.4. The resulting aqueous solution was evaporated to dryness and the resulting solid was ground up and boiled with ethanol (1 litre). The solid salt (4) was separated by centrifugation. It was then vacuum dried at 80° C. and gave an off white coloured solid 63.43 g (62.5% yield).

The material was identified as compound (4) by H nmr, and had a purity of 80%.

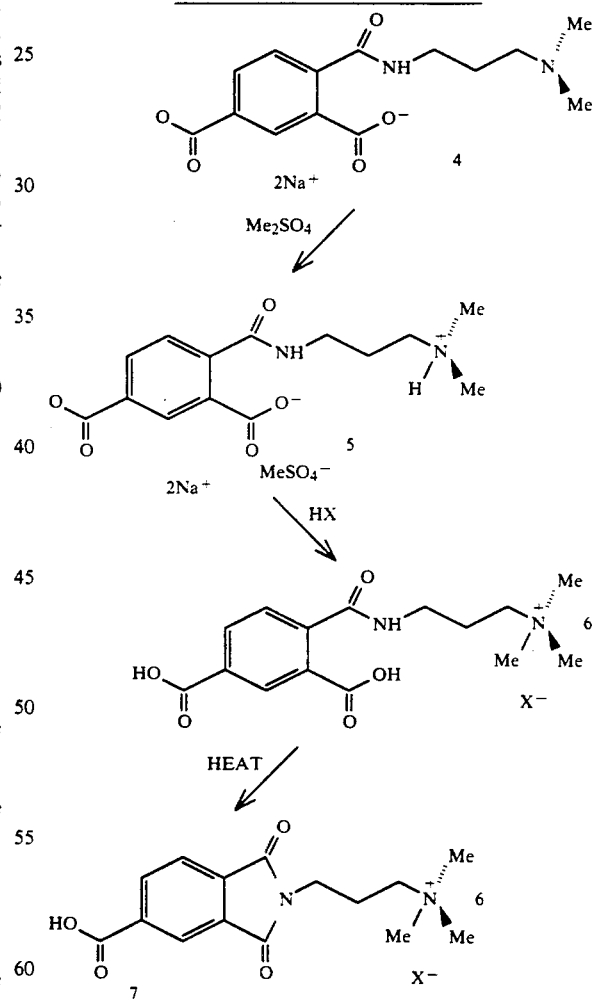

DESCRIPTION OF PROCESS 1-(3'N,N dimethyl amino propylcarbonyl) - benzene 2,3-dicarboxy disodium salt (4) (40.56 g, 0.096 mol) was dissolved in methanol (300 mls) with warming. Sufficient water was added to give a clear solution. This was then cooled to 10° C. To the cooled solution, dimethyl suphate (13.31 g, 0.1056 mol) dissolved in methanol (30 mls) was added dropwise over 15 minutes. The resulting solution was refluxed for 2½ hours and gave a clear yellow solution. The yellow solution was evaporated to dryness using an isopropylalcohol azeotrope to remove the water. The resulting yellow sticky solid (5) was boiled with ether (200 mls) and thereafter the ether decanted off; this procedure was repeated three times. The ether was evaporated to dryness and excess dimethyl sulphate was destroyed in a neutralizing solution of sodium hydroxide/ water/methylated spirits. The resulting insoluble solid was azeotroped with isopropyl alcohol to give a white powder solid (5) which was then reacted with an acid (HX) to give salt (6).

1(3′,N,N,N-Trimethylammonium propyl carbonyl)-benzene-2,3-dicarboxylate sodium salt (6), (20 g, 0.0431 mol) was dissolved in water 100 mls. This solution had a pH of pH 8.2. Toluenesulphonic acid solution was added to adjust the pH of the solution to pH 2.0. The resulting aqueous solution was evaporated to dryness using a toluene azeotrope. The resulting solid was heated with ether (100 mls) to remove any remaining toluenesulphonic acid and the ether was decanted off; this procedure was repeated three times. $^1$HNMR showed the product was a mixture of uncyclized and cyclized quaternary material.

The mixture was heated at 220° C. for ½ hour under vacuum to complete the cyclization process and thereby produced compound (7).

The product was identified by $^1$H nmr, and had a purity of 64%.

Stage 3 Synthesis of Compound 8 Scheme

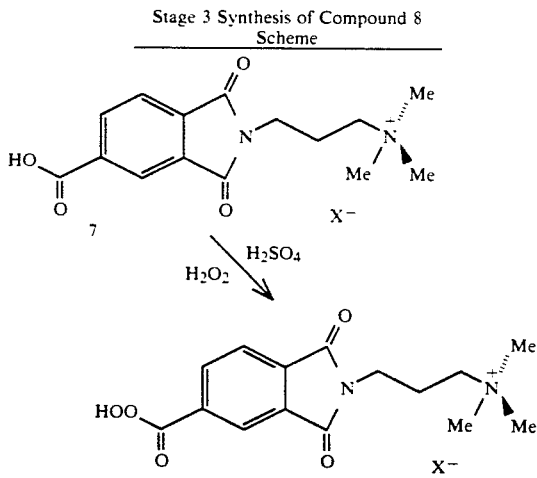

DESCRIPTION OF PROCESS

3′N,N,N,-Trimethylammonium propyl N-pthalimido-3-carboxylate hydrogen sulphate (7) (2.0 g, 0.00515 mol) was dissolved in methane sulphonic acid (15 mls) in a round-bottomed flask. The solution was cooled in ice to 5° C. and then hydrogen peroxide (0.98 mls 0.2257 mols) added dropwise over 10 minutes with stirring. The resulting mixture was left stirring in ice for 3 hours and then allowed to warm up to room temperator over 2 hours. The resulting reaction mixture was poured into ether (400 mls) and then cooled to −10° C. in acetone/solid carbon dioxide. The resulting precipitate was filtered off and washed with ether. The solid was then evaporated at room temperature to remove any residual ether. A sample was titrated and found to be 55% peroxycarboxylic acid.

The product was identified as compound (8) by $^1$H nmr.

The effectiveness of the cationic peroxycarboxylic acid of formula (IV) as a bleaching agent was examined and compared with two conventional anionic peroxyacids, namely PAP, as described in European Patent Specifications 325 289 and 325 288 and DPDA (1,12-diperoxydodecanedioic acid), described in U.S. Pat. No. 4 259 201.

Bleaching experiments were carried out with sodium perborate monohydrate on standard tea-stained test cloths.

The experiments were all carried out in a temperature-controlled glass beaker equipped with a magnetic stirrer, thermocouple and a pH electrode and at a constant temperature of 40° C. In the experiments, the peracids were dissolved in demineralised water. The acid of formula (IV) and PAP were present in the compositions at a level of 1 mmol. DPDA was present at a level of 0.5 mmol.

Four test cloths were immersed for 30 minutes in each of the compositions. After rinsing with tap water, the cloths were dried in a tumble drier. The reflectance ($R_{460}$) results presented below are an average value for four test cloths.

The results are tabulated below:

| Peracid | $\Delta R_{460}$ | | | | |
| --- | --- | --- | --- | --- | --- |
|  | pH 6 | pH 7 | pH 8 | pH 9 | pH 10 |
| Compound of formula (IV) | 25 | 22 | 21 | 12 | 8 |
| PAP | 13 | 13 | 13 | 6 | 4 |
| DPDA | 13 | 13 | 13 | 6 | 4 |

The results show that the cationic peroxycarboxylic acid of formula (IV) has a higher bleaching performance than DPDA and PAP.

We claim:

1. A peroxycarboxylic acid having the formula (I)

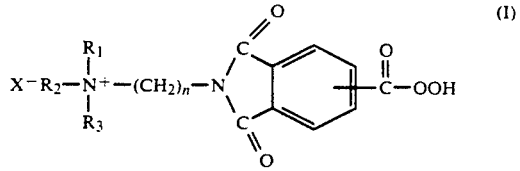

wherein $R_1$, $R_2$ and $R_3$ are each independently a $C_1$-$C_7$ alkyl group n is an integer of from 2 to 10 and X is a counter anion.

2. A peroxycarboxylic acid according to claim 1 having the formula (I′)

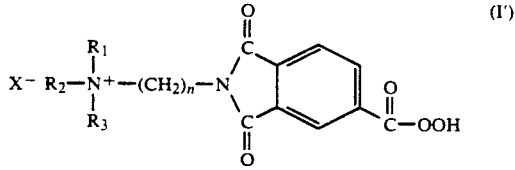

wherein $R_1$, $R_2$ and $R_3$ are each independently a $C_1$-$C_7$ alkyl group n is an integer of from 2 to 10 and X is a counter anion.

3. A peroxycarboxylic acid according to claim 1 wherein $R_1$, $R_2$ and $R_3$ are each independently $C_1$ or $C_2$ alkyl and n is an integer of from 2 to 5.

4. A peroxycarboxylic acid according to claim 1 wherein $R_1$, $R_2$ and $R_3$ are each independently $C_1$ alkyl and n is 3.

* * * * *